United States Patent
Ma (10) Patent No.: US 9,341,572 B2
(45) Date of Patent: May 17, 2016

(54) DETECTING DEVICE AND DETECTING METHOD OF A TRANSPARENT DISPLAY PANEL

(71) Applicant: BOE Technology Group Co., Ltd., Beijing (CN)

(72) Inventor: Xinli Ma, Beijing (CN)

(73) Assignee: BOE Technology Group Co., Ltd., Beijing (CN)

( * ) Notice: Subject to any disclaimer, the term of this patent is extended or adjusted under 35 U.S.C. 154(b) by 2 days.

(21) Appl. No.: 14/519,341

(22) Filed: Oct. 21, 2014

(65) Prior Publication Data

US 2016/0033405 A1 Feb. 4, 2016

(30) Foreign Application Priority Data

Aug. 1, 2014 (CN) .......................... 2014 1 0378403

(51) Int. Cl.
*G01N 21/25* (2006.01)
*G01N 21/59* (2006.01)

(52) U.S. Cl.
CPC .............. *G01N 21/59* (2013.01); *G01N 21/255* (2013.01); *G01N 2201/061* (2013.01)

(58) Field of Classification Search
CPC ......... G01N 21/59; G01N 21/255; G01J 3/02; G01J 3/50; G01J 3/51; G01J 3/10
USPC ................................................ 356/402–425
See application file for complete search history.

(56) References Cited

U.S. PATENT DOCUMENTS

2011/0007371 A1* 1/2011 Yip ........................ B41J 2/2135
358/504

FOREIGN PATENT DOCUMENTS

| CN | 101660968 A | 3/2010 |
|---|---|---|
| CN | 102928442 A | 2/2013 |
| CN | 102967443 A | 3/2013 |
| CN | 103900795 A | 7/2014 |
| JP | H08178855 A | 7/1996 |
| JP | 2001242040 A | 9/2001 |

OTHER PUBLICATIONS

Mar. 2, 2016—(CN)—First Office Action Appn No. 201410378403.X with English Tran.

* cited by examiner

*Primary Examiner* — Abdullahi Nur
(74) *Attorney, Agent, or Firm* — Banner & Witcoff, Ltd.

(57) ABSTRACT

The present disclosure relates to a detecting device and a detecting method of a transparent display panel. The method comprises: providing a reference pattern sheet having n pairs of first regions with a first color and second regions with a second color alternately arranged in a first direction, and each of the first regions and each of the second regions having a same predetermined width D in the first direction; forming a uniform predetermined illuminance on the reference pattern sheet; detecting directly the reference pattern sheet by a measuring device; detecting the reference pattern sheet through the transparent panel display by the measuring device; and thereby determining a clarity of the transparent display panel.

16 Claims, 4 Drawing Sheets

DETECTING DEVICE AND DETECTING METHOD OF A TRANSPARENT DISPLAY PANEL

This application claims priority to Chinese Patent Application No. 201410378403.X, filed on Aug. 1, 2014. The present application claims priority to and the benefit of the above-identified application and is incorporated herein in its entirety.

TECHNICAL FIELD

The present disclosure relates to a detecting device and a detecting method of a transparent display panel.

BACKGROUND

With development of information technology, the transparent display technology increasingly attracts people's attention. A transparent display panel has a certain transparency, that is, the transparent display panel can display information upon operation, and the user can also see the background through the transparent display panel when the transparent display panel does not display any information. The transparent display panel can be applied to building external walls, showcases, vending machines or car windows to provide contents such as advertising or graphical interface.

SUMMARY

The present disclosure provides a detecting device and a detecting method of a transparent display panel, and thus a rapid detection of the transparency of the transparent display panel is realized.

A detecting method according to the present disclosure comprises: providing a reference pattern sheet having a plurality of first regions and a plurality of second regions alternately arranged in a first direction, each of the first regions having a first color, each of the second regions having a second color different from the first color, each of the first regions and each of the second regions having a same predetermined width D in the first direction, and the reference pattern sheet having n pairs of the first regions and the second regions in the first direction; forming a uniform predetermined illuminance on the reference pattern sheet by irradiating the reference pattern sheet with a light source; detecting directly the reference pattern sheet by a measuring device separated from the reference pattern sheet by a predetermined distance so as to obtain a value measured without panel $D_{Pi}$ of a sum of the predetermined widths of each pair of the first region and the second region of the reference pattern sheet; placing the transparent panel display between the measuring device and the reference pattern sheet; detecting the reference pattern sheet through the transparent display panel without displaying an image by the measuring device so as to obtain a first value measured with panel $D_{1i}$ of the predetermined width of each first region of the reference pattern sheet and a second value measured with panel $D_{2i}$ of the predetermined width of each second region of the reference pattern sheet, where i=1, ..., n, and n is a positive integer; and determining a clarity C of the transparent display panel according to a ratio of a sum of each pair of the first value measured with panel $D_{1i}$ and the second value measured with panel $D_{2i}$ to the value measured without panel $D_{Pi}$ of the sum of the predetermined widths of each pair of the first region and the second region, wherein the clarity C of the transparent display panel is linearly proportional to the ratio.

A detecting device according to the present disclosure comprises: a reference pattern sheet having first regions and second regions alternately arranged in a first direction, each of the first regions having a first color, each of the second regions having a second color different from the first color, each of the first regions and each of the second regions having a same predetermined width D in the first direction, and the reference pattern sheet having n pairs of the first regions and the second regions in the first direction; a light source irradiating the reference pattern sheet to form a uniform predetermined illuminance on the reference pattern sheet; a measuring device arranged to be separated from the reference pattern sheet by a predetermined distance and detecting measured values of the widths of each first region and each second region of the reference pattern sheet in the first direction, wherein the measured values comprise: a value measured without panel $D_{Pi}$ of a sum of the predetermined widths of each pair of the first region and the second region in a case that no transparent display panel is provided between the measuring device and the reference pattern sheet, and each pair of a first value measured with panel $D_{1i}$ of the predetermined width of each first region of the reference pattern sheet in a case that a transparent display panel without displaying an image is placed between the measuring device and the reference pattern sheet and a second value measured with panel $D_{2i}$ of the predetermined width of each second region of the reference pattern sheet in the case that the transparent display panel without displaying an image is placed between the measuring device and the reference pattern sheet, where i=1, ..., n, and n is a positive integer; a holding device arranged between the measuring device and the reference pattern sheet and configured to place the transparent display panel between the measuring device and the reference pattern sheet or remove the transparent display panel between the measuring device and the reference pattern sheet; and an evaluation device configured to determine a clarity C of the transparent display panel according to a ratio of a sum of each pair of the first value measured with panel $D_{1i}$ and the second value measured with panel $D_{2i}$ to the value measured without panel $D_{Pi}$ of the sum of the predetermined widths of each pair of the first region and the second region, wherein the clarity C of the transparent display panel is linearly proportional to the ratio.

According to one example of the present disclosure, the clarity C of the transparent display panel is determined by following formulas:

$$K = \left(\frac{\sum_{i=1}^{n} D_{Pi}}{n}\right) \times \frac{1}{2D},$$

where K is an influence factor;

$$C = \frac{\sum_{i=1}^{n}\left(\frac{D_{1i}}{K} + \frac{D_{2i}}{K}\right)}{2n} \times \frac{1}{D} \times 100\%.$$

According to one example of the present disclosure, the reference pattern sheet has a stripe pattern with each of the first regions and the each of second regions having a strip-shape pattern extending along a second direction perpendicular to the first direction, a target-shape pattern with alternately nested annular first regions and second regions, or a chessboard pattern with first regions and second regions alternately arranged in the first direction and the second direction, or a grid pattern.

According to one example of the present disclosure, the first color has a gray scale different from that of the second color.

According to one example of the present disclosure, the first color is black, red, blue or green, and the second color is white, yellow or pink. A brightness value curve of the reference pattern sheet is obtained by the measuring device. Amplitude of the brightness value curve is obtained by a difference between an average maximum and an average minimum of the brightness value curve. The first value measured with panel $D_{1i}$ of each first region is determined by a first brightness value obtained by a sum of 10% of the amplitude and the average minimum, and the second value measured with panel $D_{2i}$ of each second region is determined by a second brightness value obtained by a sum of 90% of the amplitude and the average minimum. The value measured without panel $D_{Pi}$ of the sum of the predetermined widths of each pair of the first region and the second region is determined by the first brightness value or the second brightness value.

According to one example of the present disclosure, the influence factor K is depended on the predetermined illuminance on the reference pattern sheet, the pattern of the reference pattern sheet, and the predetermined distance between the reference pattern sheet and the measuring device.

According to one example of the present disclosure, the light source is a standard light source comprising D65、D75、D50、TL83、TL84、 CWF、U30、U35、F、A、B or C.

According to one example of the present disclosure, the measuring device comprises a CCD, a spectrometer or an integrating sphere.

BRIEF DESCRIPTION OF THE DRAWINGS

In order to clearly illustrate the technical solution of the present disclosure, the technical solution of the present disclosure will be further described with reference to the following drawings. The drawings described in the following are only related to a part of embodiments of the technical solution of the present disclosure.

DETAILED DESCRIPTION OF THE PREFERRED EMBODIMENTS

The technical solution of the embodiments of the present disclosure will be described clearly and fully in connection with the drawings of the embodiments of the present disclosure. It is obvious that the described embodiments are just a part but not all of the embodiments of the present disclosure. Based on the described embodiments of the present disclosure, those skilled in the art can obtain all other embodiment without any inventive work, which all fall into the scope of the claimed invention.

Unless otherwise defined, technical terms or scientific terms used herein shall have a common meaning known by those skilled in the art of the present disclosure. Words and expressions such as "first", "second" and the like used in the description and claims of the patent application of the present disclosure do not denote any sequence, quantity or importance, but distinguish different components. Likewise, words such as "a", "an" and the like do not denote quantitative restrictions, but denote the presence of at least one. Words such as "connected", "connecting" and the like are not restricted to physical or mechanical connections, but may include electrical connections, regardless of direct or indirect connections. Words such as "up", "below", "left", "right", etc., are only used to denote the relative positional relationship. Upon the absolute position of the described object changes, the relative positional relationship change correspondingly.

Transparent effect of a transparent display panel refers to a degree of clarity of an object observed by human eyes through the transparent panel. At present, there is no uniform test method and test standard for the transparent effect of the transparent display panel.

The transparency of a transparent material is usually characterized by haze value. Haze is a ratio of scattering transmissivity $\tau_d$ of the transparent material to total transmissivity $\tau_t$ thereof, which is expressed as a percentage. If the haze of the transparent material is indicated by H, $$H=\tau_d/\tau_t \times 100\% \tag{1}$$

The haze value H of the transparent material is usually in a range of 0~30%.

Figure 1:
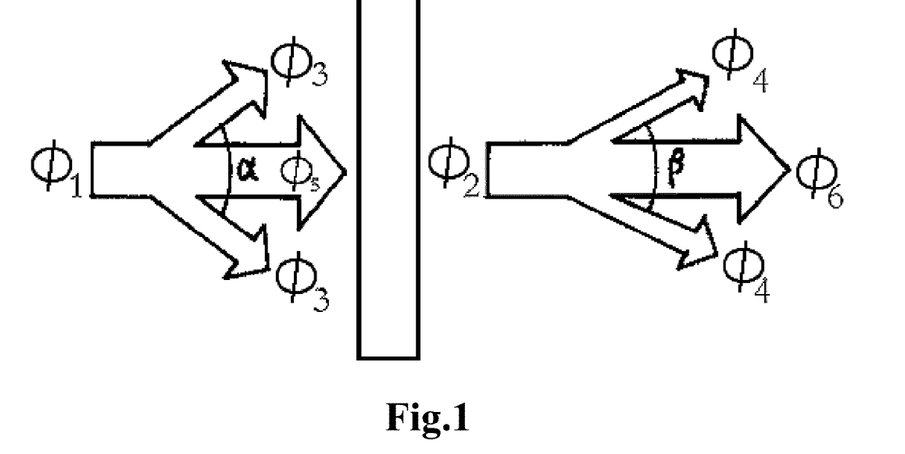
FIG. 1 is a schematic view showing principles for measuring haze.

Generally, the haze value of the transparent material is measured by a haze measuring device. In case that the haze H of the transparent material is measured, incident light beam perpendicularly incident on a surface of a test sample is a substantially collimated light beam with a light flux of $\Phi_1$. Most of the light flux of the beam $\Phi_1$ is centralized within a divergence angle $\alpha$ of 6°, and is called straight incident light flux part $\Phi_5$. An extremely tiny part of the light flux deviating beyond the divergence angle $\alpha$ in $\Phi_1$ is a scattering incident light flux part $\Phi_3$. Referring to FIG. 1, the relationship between $\Phi_1$ and $\Phi_3$, $\Phi_5$ is as follows.

$$\Phi_1=\Phi_3+\Phi_5 \tag{2}$$

$\Phi_1$ is transmitted through the test sample to form a total transmitted light flux $\Phi_2$. Most of $\Phi_2$ is centralized in a divergence angle $\beta$ of 5°, and is called straight transmitted light flux part $\Phi_6$. A small part of the transmitted light flux deviates beyond the divergence angle $\beta$ and is called scattering transmitted light flux $\Phi_4$. The relationship between $\Phi_2$ and $\Phi_4$, $\Phi_6$ is as follows.

$$\Phi_2=\Phi_4+\Phi_6 \tag{3}$$

According to the definition of transmissivity, the total transmissivity $\tau_t$ is equal to:

$$\tau_t=\Phi_2/\Phi_1 \tag{4}$$

The scattering transmissivity $\tau_d$ is equal to:

$$\tau_d=(\Phi_4-\Phi_3\cdot\tau_t)/\Phi_1 \tag{5}$$

The calculating formula of the haze H of the test sample indicated by $\Phi_1$, $\Phi_2$, $\Phi_3$ and $\Phi_4$ is obtained by substituting the two formulas (4) and (5) into the formula (1).

$$H=\Phi_4/\Phi_2-\Phi_3/\Phi_1 \qquad (6)$$

Figure 2:
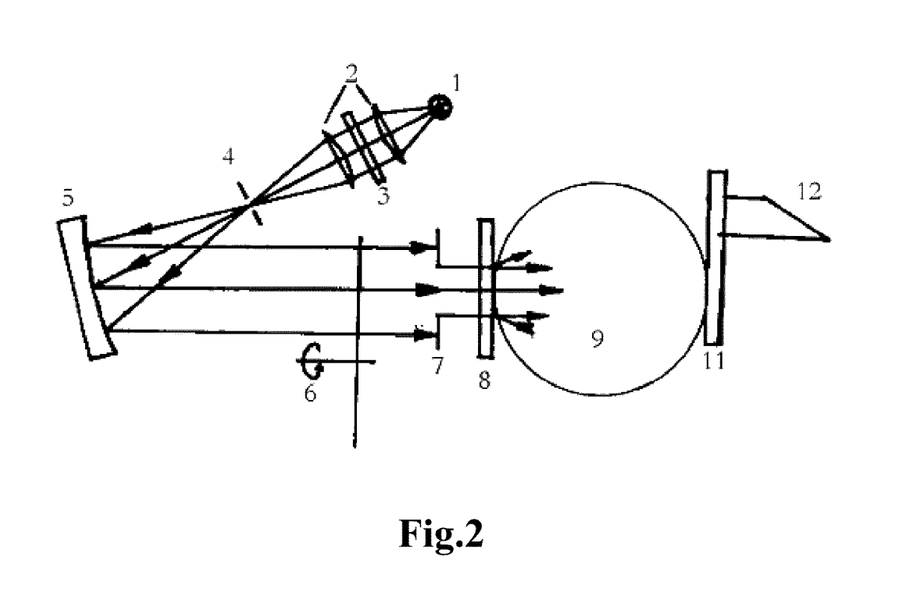
FIG. 2 is a schematic view of a light path of a measuring device of haze.

FIG. 2 is a schematic view of a light path of a measuring device of haze. The measuring device of haze mainly comprises a light source 1; a relay optical system for forming a collimated light beam composed of a lens 2, a stop 4, a mirror 5, a modulator and a stop 7; a sample holder 8 for holding a test sample; and a measuring system comprising an integrating sphere for measuring light 9, a diode 10, a slider 11, and an optical trap 12.

The optical system of the above measuring device of haze is complex, and thus is not suitable for rapid detection of the transparency of mass-produced transparent display panels.

The present disclosure provides a detecting device and a detecting method of a transparent display panel, and thus a rapid detection of the transparency of the transparent display panel without displaying an image is realized.

Figure 3:
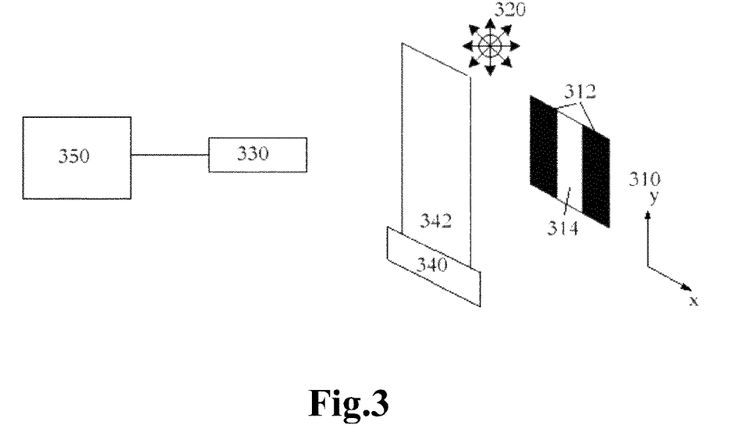
FIG. 3 is a schematic view of a detecting device of a transparent display panel according to the present disclosure.

FIG. 3 is a schematic view of a detecting device of a transparent display panel of an embodiment according to the present disclosure. The detecting device 300 comprises a reference pattern sheet 310, a light source 320, a measuring device 330, a holding device 340 and an evaluation device 350.

The reference pattern sheet 310 has first regions 312 and second regions 314 alternately arranged in a first direction x. Each of the first regions 312 has a first color. Each of the second regions 314 has a second color different from the first color. For example, the first color has a gray scale different from that of the second color. As in the example illustrated in FIG. 3, the first color of each first region 312 is black, and the second color of each second region 314 is white. If the gray scale value is defined in the range of L0~L255, the gray scale value of black is set to L0, and the gray scale value of white is set to L255. The first color of each first region 312 and the second color of each second region 314 are not limited thereto. For example, the first color can be blue, green, red or the like, and the second color can be yellow, pink or the like so that there is a substantial difference between the gray scale values of the first color and the second color. Each of the first regions 312 and each of the second regions 314 have a same predetermined width D in the first direction x. The reference pattern sheet 310 has n pairs of the first regions 312 and the second regions 314 in the first direction x. In FIG. 3, both of the first region 312 and the second region 314 in the reference pattern sheet 310 have a strip-shape extending along a second direction y perpendicular to the first direction x.

Figure 4:
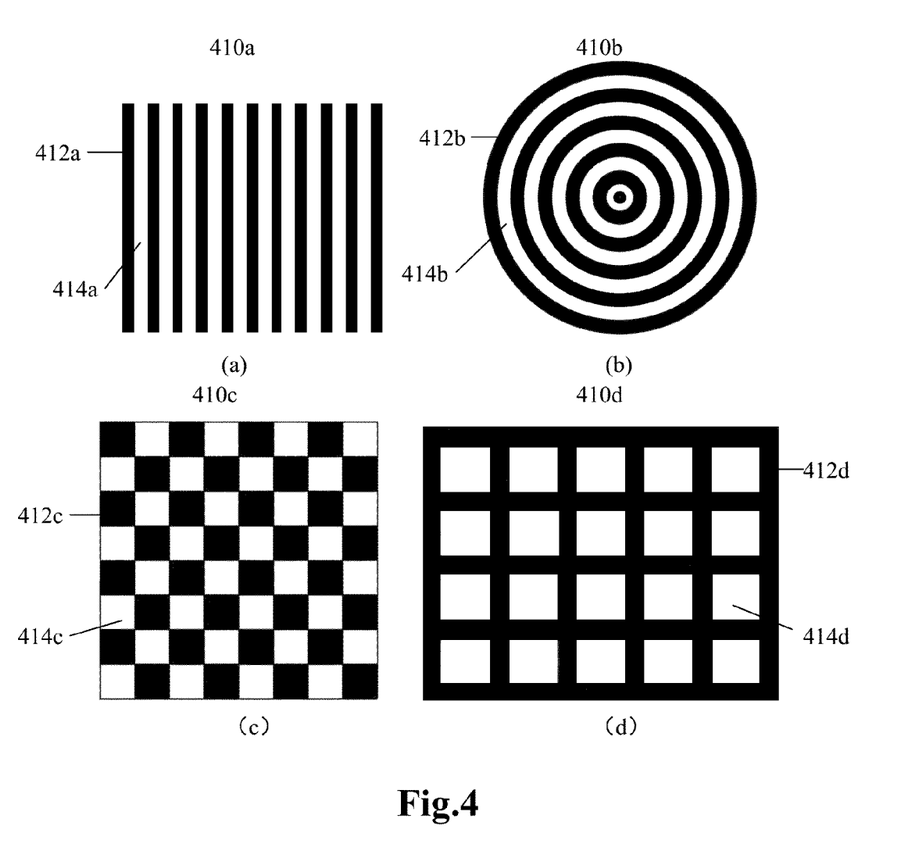
FIG. 4 is a schematic view of examples of reference pattern sheets used in a detecting device of a transparent display panel according to the present disclosure.

The reference pattern sheet can have other patterns. FIG. 4 is a schematic view of several examples of the reference pattern sheet. As illustrated in FIG. 4(a), the reference pattern sheet 410a is a commercially available standard board for visual measurement which is similar to the reference pattern sheet illustrated in FIG. 3, for example, a single-frequency Ronchi grating pattern. The single-frequency Ronchi grating pattern comprises black rectangular stripes 412a uniformly arranged in one direction with white second regions 414a provided between the rectangular stripes 412a. As illustrated in FIG. 4(b), the first regions 412b and the second regions 414b in the reference pattern sheet 410b have nested annular shapes so that the reference pattern sheet 410b has a target-shape pattern as a whole. In addition, the first regions 412b and the second regions 414b of the reference pattern sheet 410b also can be nested hexagonal or nested octagonal shapes, etc. As illustrated in FIG. 4(c), the first regions 412c and the second regions 414c in the reference pattern sheet 410c are squares alternately arranged in two directions which are perpendicular to each other, and thus the reference pattern sheet 410c has a chessboard pattern as a whole. As illustrated in FIG. 4(d), the first regions 412d in the reference pattern sheet 410d have an overall orthogonal grid structure, and the second regions 414d are blank regions between the grid structure. However, the reference pattern sheets used in the present disclosure are not limited thereto.

As illustrated in FIG. 3, a light source 320 irradiates the reference pattern sheet 310 so as to form a uniform predetermined illuminance, for example, about 500 lux, on the reference pattern sheet 310. The light source 320 can use a standard light source. For example, the standard light source comprises D65 (International Standard Artificial Daylight with a color temperature of 6500K), D75 (Simulated Northern Average Sunlight with a color temperature of 7500K), D50 (simulated sunlight with a color temperature of 5000K), TL83 (European Standard Warm White Store Light with a color temperature of 5000K), TL84 (Simulated European Store Light with a color temperature of 4000K), TL84 (European, Japanese, Chinese Store Light with a color temperature of 4000K), CWF (American Cool White Fluorescent with a color temperature of 4100K), U30 (American Warm White Fluorescent with a color temperature of 3000K), U35 (Color Light Designated by USA Retailer Target with a color temperature of 3500K), F (Home and Hotel Light with a color temperature of 2700K), A (American Show Window Light with a color temperature of 2856K), B (direct sunlight with a color temperature of 4878K) or C (approximate cloudy sky daylight with a color temperature of 6774K). The transparency of the transparent display panel can be determined in the case of simulation of the actual operational environment of this transparent display panel by selecting at least one of the above standard light sources, and thus more accurate results are obtained.

The light source 320 is arranged on a side of the reference pattern sheet 310 at a predetermined distance from the reference pattern sheet 310, and thus a uniform predetermined illuminance is formed on the reference pattern sheet 310. The predetermined illuminance is about 500 lux, for example. In the present embodiment, the number of the light source 320 is not limited to one. The measuring device 330 also can have a plurality of light source 320 uniformly distributed around the reference pattern sheet 310 to improve the uniformity of the illuminance on the reference pattern sheet 310 It is noted that the positions of the light source 320 should not affect the detection of the reference pattern sheet 310 by the measuring device 330.

As illustrated in FIG. 3, the measuring device 330 is separated from the reference pattern sheet 310 by a predetermined distance. The measuring device 330 is configured to detect measured values of the widths of each first region 312 and each second region 314 of the reference pattern sheet in the first direction x. For example, the measuring device 330 comprises optical sensors such as a CCD, a spectrometer, an integrating sphere or the like. For example, the measuring device 330 can be separated from the reference pattern sheet 310 by 100 cm.

As illustrated in FIG. 3, the holding device 340 is arranged between the measuring device 330 and the reference pattern sheet 310, and is configured to place a transparent display panel 342 in a light path between the measuring device 330 and the reference pattern sheet 310 or remove the transparent display panel out of the light path between the measuring device 330 and the reference pattern sheet 310. For example, the transparent display panel 342 is arranged at a distance of 50 cm from the reference pattern sheet 310 by the holding device 340. The holding device 340 can be a bracket or a clamp for holding the transparent display panel, which can be moved by a driver (not shown).

As illustrated in FIG. 3, the evaluation device 350 of the detecting device 300 is connected to the measuring device 330, and records the measured values of the widths of each first region 312 and each second region 314 of the reference pattern sheet in the first direction x obtained by the measuring device 330. The measured values comprise: a measured value without panel $D_{Pi}$ of a sum of the predetermined widths of each pair of the first region and the second region in a case that the transparent display panel 342 is not provided between the measuring device 330 and the reference pattern sheet 310; a first value measured with panel $D_{1i}$ of the predetermined width of each first region 312 of the reference pattern sheet in a case that the transparent panel display 342 having no image displayed is placed between the measuring device 330 and the reference pattern sheet 310; and a second value measured with panel $D_{2i}$ of the predetermined width of each second region 314 of the reference pattern sheet 310 in the case that the transparent panel display 342 having no image displayed is placed between the measuring device 330 and the reference pattern sheet 310, where i=1, . . . , n, and n is a positive integer. The evaluation device determines a clarity C of the transparent display panel according to a ratio of a sum of each pair of the first value measured with panel $D_{1i}$ and the second value measured with panel $D_{2i}$ to the value measured without panel $D_{Pi}$. The clarity C of the transparent display panel is linearly proportional to the ratio.

In one example, the clarity C of the transparent display panel 342 can be calculated according to following formulas:

$$K = \left(\frac{\sum_{i=1}^{n} D_{Pi}}{n}\right) \times \frac{1}{2D}; \quad (7)$$

$$C = \frac{\sum_{i=1}^{n}\left(\frac{D_{1i}}{K} + \frac{D_{2i}}{K}\right)}{2n} \times \frac{1}{D} \times 100\%. \quad (8)$$

where K is an influence factor of the detecting device.

The evaluation device 350 can be a computer or a computer module.

The clarity C can be from 0% to 100%. The larger the value of the clarity C is, the better the transparency of the corresponding transparent display panel is.

An operating method of the detecting device 300 is further explained below in combination with a detecting method of a transparent display panel according to the present disclosure.

Figure 5:
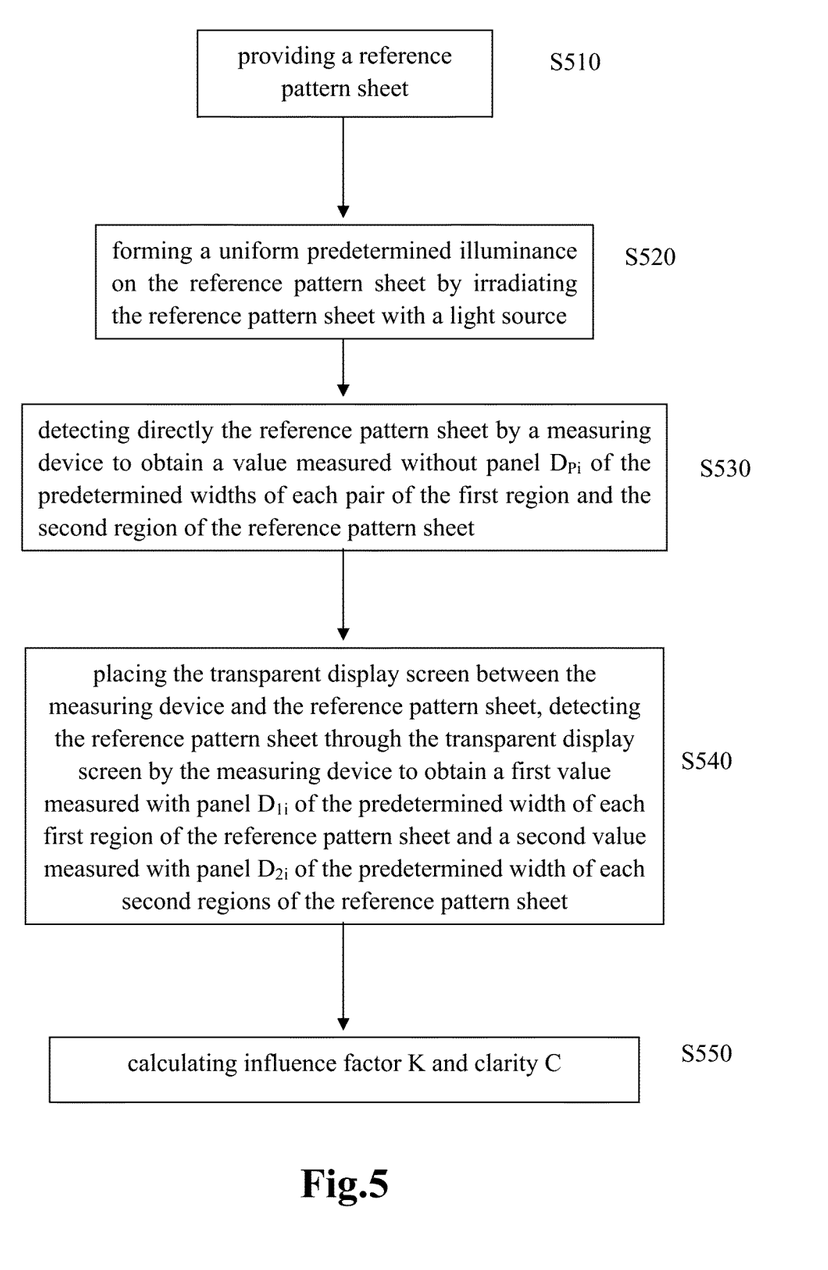
FIG. 5 is a flowchart of a detecting method of a transparent display panel according to the present disclosure.

FIG. 5 is a flowchart of a detecting method of a transparent display panel according to the present disclosure. As illustrated in FIG. 5, the detecting method of the transparent display panel according to an embodiment of the present disclosure comprises following steps.

Firstly, in step S510, a reference pattern sheet is provided. The reference pattern sheet has a plurality of first regions and a plurality of second regions alternately arranged in a first direction. Each of the first regions has a first color, and each of the second regions has a second color which is different from the first color. Each of the first regions and each of the second regions have a same predetermined width D in the first direction. The reference pattern sheet has n pairs of the first regions and the second regions in the first direction. The details of reference pattern sheet can be referred to the reference pattern sheets 310, and 410*a-d* described in FIG. 3 and FIG. 4, which will not be repeated herein. The structure of the reference pattern sheet is not limited to the patterns illustrated in the above figures.

Secondly, in step S520, a uniform predetermined illuminance is formed on the reference pattern sheet by irradiating the reference pattern sheet with a light source.

Next, in step S530, the reference pattern sheet is detected directly by a measuring device separated from the reference pattern sheet so as to obtain a value measured without panel $D_{Pi}$ of a sum of the predetermined widths of each pair of the first region and the second region of the reference pattern sheet. In this step, there is no transparent display panel placed in a light path between the reference pattern sheet and the measuring device.

In step S540, a transparent display panel is placed between the measuring device and the reference pattern sheet. The transparent display panel can be placed by a holding device described as above. To this end, the reference pattern sheet is detected through the transparent display panel by the measuring device so as to obtain a first value measured with panel $D_{1i}$ of the predetermined width of each first region of the reference pattern sheet and a second value measured with panel $D_{2i}$ of the predetermined width of each second region of the reference pattern sheet. In this step, the transparent display panel does not display any image, and thus the reference pattern sheet behind the transparent display panel can be detected by the measuring device.

The order of the above steps S530 and S540 can be interchanged.

In step S550, a clarity C of the transparent display panel is determined by an evaluation device according to a ratio of a sum of each pair of the first value measured with panel $D_{1i}$ and the second value measured with panel $D_{2i}$ to the value measured without panel $D_{Pi}$. The clarity C of the transparent display panel is linearly proportional to the ratio.

For example, in step S550, based on the value measured without panel $D_{Pi}$ of the sum of the predetermined widths of each pair of the first region and the second region, an influence factor K can be obtained by calculation according to the above formula (7). The influence factor K is dependent on the predetermined illuminance on the reference pattern sheet, the pattern of the reference pattern sheet, the predetermined distance between the reference pattern sheet and the measuring device, and settings of the measuring device, etc. The calculation of the influence factor K also can be performed immediately after the step S530.

Then, in step S550, the clarity C of the transparent display panel is calculated by the evaluation device, based on the influence factor K, the first value measured with panel $D_{1i}$ of the predetermined width of each first region of the reference pattern sheet and the second value measured with panel $D_{2i}$ of the predetermined width of each second region of the reference pattern sheet according to the above formula (8). By introducing the influence factor K in the calculation of the clarity C, the adverse effect on the stability and reliability of the detection induced by the settings of respective components of the measuring device and environmental factors can be eliminated.

Figure 6:
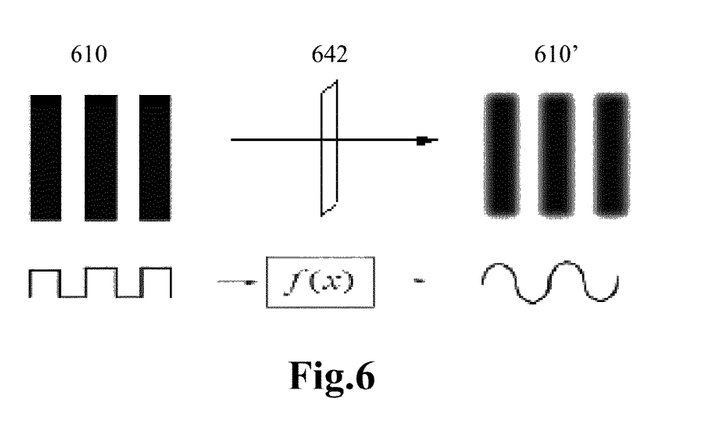
FIG. 6 is a schematic view showing principles for the detecting method of a transparent display panel according to the present disclosure.

A detecting method according to the present disclosure is further explained below in combination with an example illustrated in FIG. 6 and FIG. 7. FIG. 6 is a schematic view showing principles for one example of a detecting method of a transparent display panel according to the present disclosure. In the example shown in FIG. 6, a reference pattern sheet 610 having alternated black-white stripes is used. If transparency of a transparent display panel 642 arranged in the light path between the measuring device and the reference pattern sheet 610 is low, a measured pattern 610' of the reference pattern sheet detected by the measuring device, for example, a CCD camera, will have a blurred contour or a blurred edge. Thus, a brightness curve obtained by the measuring device also have a transitional region between the first region and the second region with different gray values, resulting in a transition of the brightness curve from an ideal rectangular shape to a shape similar to the sine wave.

Figure 7:
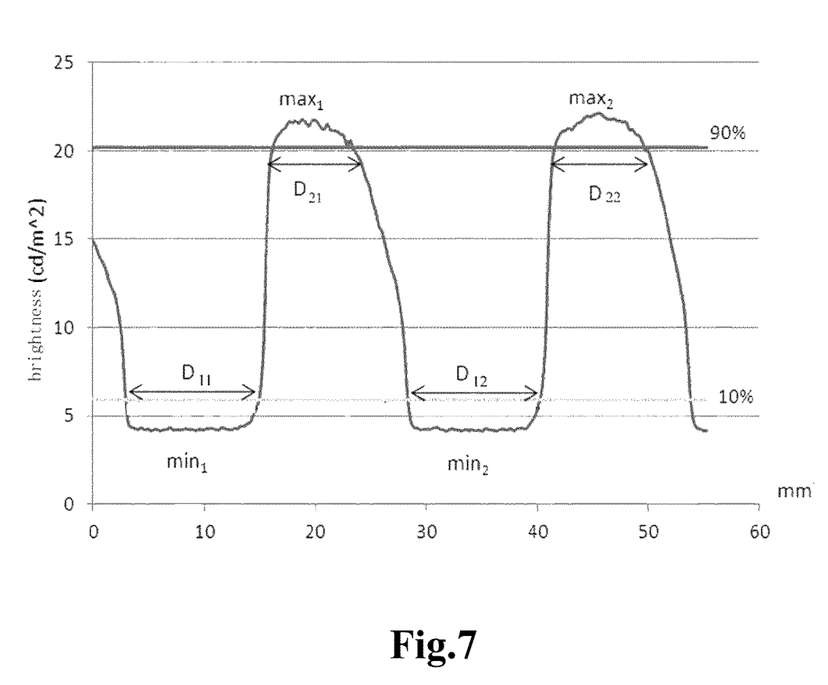
FIG. 7 is a partial a brightness curve obtained in one example of a detecting method of a transparent display panel according to the present disclosure.

FIG. 7 is a part of a brightness curve obtained in one example of a detecting method of a transparent display panel according to the present disclosure, which characterizes the variation of the brightness of the detected reference pattern sheet in the width direction of the reference pattern sheet. In combination with FIG. 7, it is now described how to determine measured values $D_{1i}$ and $D_{2i}$ of respective widths in the reference pattern sheet. It is assumed that a first color of each first region of the reference pattern sheet is black, red, blue or green, and a second color of each second region is white, yellow or pink, the brightness curve as illustrated in FIG. 7 can be obtained in the step S540. This brightness curve has a plurality of maxima $max_i$, such as $max_1$ and $max_2$ illustrated in FIG. 7, and a plurality of minima $min_i$, such as $min_1$ and $min_2$ illustrated in FIG. 7. An average maximum, i.e. an arithmetic mean value of a plurality of maxima, and an average minimum, i.e. an arithmetic mean value of a plurality of minima are calculated by an evaluation device. A difference between this average maximum and this average minimum is the amplitude of this brightness curve. By intersecting this brightness curve with a transverse straight line representing a first brightness value of a sum of 10% of this amplitude and the average minimum, the measured values of the width of each first region, for example, first values measured with panel $D_{11}$ and $D_{12}$, can be determined according to a difference between two dimension values at the intersections of each trailing edge and a subsequent rising edge of the brightness curve on this transverse straight line representing the first brightness value. By intersecting this brightness curve with a transverse straight line representing a second brightness value obtained by a sum of 90% of this amplitude and the average minimum, the measured values of the width of each second region, for example, second values measured with panel $D_{21}$ and $D_{22}$, can be determined according to a difference between two dimension values at the intersections of each rising edge and a next trailing edge of the brightness curve on this transverse straight line representing the second brightness value. Those skilled in the art can also determine the measured values $D_{1i}$, $D_{2i}$ and $D_{Pi}$ of corresponding widths by selecting other values other than 10% and 90% based on the brightness curve.

In addition, the measured value without panel $D_{Pi}$ of the sum of the predetermined widths of each pair of the first region and the second region can be determined based on either the first brightness value or the second brightness value. For example, By intersecting a brightness curve obtained in the step S530 without panel with a transverse straight line representing the first brightness value, the measured value without panel $D_{Pi}$ of the sum of the widths of each pair of the first region and the second region can be determined according to a difference between two dimension values at the intersections of each trailing edge and a subsequent trailing edge of this brightness curve on this transverse straight line representing the first brightness value. Alternatively, by intersecting this brightness curve with a transverse straight line representing the second brightness value, the measured value without panel $D_{Pi}$ of the sum of the widths of each pair of the first region and the second region can be determined according to a difference between two dimension values at the intersections of each rising edge and a subsequent rising edge of the brightness curve on this transverse straight line representing the second brightness value.

In a method of the present disclosure, the influence factor K is depended on the predetermined illuminance on the reference pattern sheet, the pattern of the reference pattern sheet, the predetermined distance between the reference pattern sheet and the measuring device, and settings of the measuring device, etc. By introducing the influence factor K in the calculation of the clarity C, the adverse effect on the stability and reliability of the detection induced by the settings of respective components of the measuring device and environmental factors can be eliminated. Thus, in the method of the present disclosure, the above detection conditions will be kept the same in both cases with the panel and without the panel and thus a reliable result can be obtained. Moreover, upon different transparent display panels are compared, it is also required to maintain the distance between the transparent display panel and the reference pattern sheet the same to obtain a reliable comparison.

A transparent display panel of the present disclosure comprises a liquid transparent display panel, an OLED transparent display panel, etc.

According to the detecting method and the detecting device of the transparent display panel of the present disclosure, a rapid detection of the transparency of the transparent display panel is realized.

The foregoing detailed description of the invention has been presented for purposes of illustration and description. It is not intended to be exhaustive or to limit the invention to the precise form disclosed. Many modifications and variations are possible in light of the above teaching. The described embodiments were chosen in order to best explain the principles of the invention and its practical application to thereby enable the skilled in the art to best utilize the invention in various embodiments and with various modifications as are suited to the particular use contemplated. It is intended that the scope of the invention be defined by the claims appended hereto.

What is claimed is:

1. A detecting method of a transparent display panel, comprising:
    providing a reference pattern sheet having a plurality of first regions and a plurality of second regions alternately arranged in a first direction, wherein each of the first regions has a first color, each of the second regions has a second color different from the first color, each of the first regions and each of the second regions have a same predetermined width D in the first direction, and the reference pattern sheet has n pairs of the first regions and the second regions in the first direction;
    forming a uniform predetermined illuminance on the reference pattern sheet by irradiating the reference pattern sheet with a light source;
    detecting directly the reference pattern sheet by a measuring device separated from the reference pattern sheet by a predetermined distance so as to obtain a value measured without panel DPi of a sum of the predetermined widths of each pair of the first region and the second region of the reference pattern sheet, where i=1, ..., n, and n is a positive integer;
    placing the transparent display panel between the measuring device and the reference pattern sheet;
    detecting the reference pattern sheet through the transparent display panel having no image displayed by the measuring device so as to obtain a first value measured with panel D1i of the predetermined width of each first region of the reference pattern sheet and a second value measured with panel D2$i$ of the predetermined width of each second regions of the reference pattern sheet, where i=1, . . . , n; and determining a clarity C of the transparent display panel according to a ratio of a sum of each pair of the first value measured with panel D1$i$ and the second value measured with panel D2$i$ to the value measured without panel DP$i$ of the sum of the predetermined widths of each pair of the first region and the second region, wherein the clarity C of the transparent display panel is linearly proportional to the ratio.

2. The detecting method according to claim 1, wherein the clarity C of the transparent display panel is determined by following formulas:

$$K = \left(\frac{\sum_{i=1}^{n} D_{Pi}}{n}\right) \times \frac{1}{2D},$$

where K is an influence factor;

$$C = \frac{\sum_{i=1}^{n}\left(\frac{D_{1i}}{K} + \frac{D_{2i}}{K}\right)}{2n} \times \frac{1}{D} \times 100\%.$$

3. The detecting method according to claim 1, wherein the reference pattern sheet has a stripe pattern with each of the first regions and the each of second regions having a strip-shape pattern extending along a second direction perpendicular to the first direction, a target-shape pattern with alternately nested annular first regions and second regions, or a chessboard pattern with first regions and second regions alternately arranged in the first direction and the second direction, or a grid pattern.

4. The detecting method according to claim 1, wherein the first color has a gray scale different from that of the second color.

5. The detecting method according to claim 4, wherein the first color is black, red, blue or green, and the second color is white, yellow or pink.

6. The detecting method according to claim 5, wherein a brightness value curve of the reference pattern sheet is obtained by the measuring device, an amplitude of the brightness value curve is obtained by a difference between an average maximum and an average minimum of the brightness value curve, the first value measured with panel D1$i$ of each first region is determined by a first brightness value obtained by a sum of 10% of the amplitude and the average minimum, and the second value measured with panel D2$i$ of each second region are determined by a second brightness value obtained by a sum of 90% of the amplitude and the average minimum, and the value measured without panel DP$i$ of the predetermined widths of each pair of the first region and the second region is determined by the first brightness value or the second brightness value.

7. The detecting method according to claim 1, wherein the influence factor K is depended on the predetermined illuminance on the reference pattern sheet, the pattern of the reference pattern sheet, the predetermined distance between the reference pattern sheet and the measuring device, and settings of the measuring device.

8. A detecting device of a transparent display panel, comprising:

a reference pattern sheet having first regions and second regions alternately arranged in a first direction, wherein each of the first regions has a first color, each of the second regions has a second color different from the first color, each of the first regions and each of the second regions have a same predetermined width D in the first direction, and the reference pattern sheet has n pairs of the first regions and the second regions in the first direction;

a light source for irradiating the reference pattern sheet so as to form a uniform predetermined illuminance on the reference pattern sheet;

a measuring device arranged to be separated from the reference pattern sheet by a predetermined distance, and detecting measured values of widths of each first region and each second region of the reference pattern sheet in the first direction, wherein the measured values comprise: a value measured without panel $D_{Pi}$ of a sum of the predetermined widths of each pair of the first region and the second region in a case that no transparent display panel is provided between the measuring device and the reference pattern sheet, and each pair of a first value measured with panel $D_{1i}$ of the predetermined width of each first region of the reference pattern sheet and a second value measured with panel $D_{2i}$ of the predetermined width of each second region of the reference pattern sheet in the case that the transparent display panel without displaying an image is placed between the measuring device and the reference pattern sheet, where i=1, . . . , n, and n is a positive integer;

a holding device arranged between the measuring device and the reference pattern sheet and configured to place the transparent display panel into a position between the measuring device and the reference pattern sheet or remove the transparent display panel from the position between the measuring device and the reference pattern sheet; and an evaluation device configured to determine a clarity C of the transparent display panel according to a ratio of a sum of each pair of the first value measured with panel $D_{1i}$ and the second value measured with panel $D_{2i}$ to the value measured without panel $D_{Pi}$ of the sum of the predetermined widths of each pair of the first region and the second region, wherein the clarity C of the transparent display panel is linearly proportional to the ratio.

9. The detecting device according to claim 8, wherein the clarity C of the transparent display panel is determined by following formulas:

$$K = \left(\frac{\sum_{i=1}^{n} D_{Pi}}{n}\right) \times \frac{1}{2D},$$

where K is an influence factor of the detecting device;

$$C = \frac{\sum_{i=1}^{n}\left(\frac{D_{1i}}{K} + \frac{D_{2i}}{K}\right)}{2n} \times \frac{1}{D} \times 100\%.$$

10. The detecting device according to claim 8, wherein the reference pattern sheet has a stripe pattern with each of the first regions and the each of second regions having a strip-shape pattern extending along a second direction perpendicular to the first direction, a target-shape pattern with alternately nested annular first regions and second regions, or a chessboard pattern with first regions and second regions alternately arranged in the first direction and the second direction, or a grid pattern.

11. The detecting device according to claim 8, wherein the first color has a gray scale different from that of the second color.

12. The detecting device according to claim 11, wherein the first color is black, red, blue or green, and the second color is white, yellow or pink.

13. The detecting device according to claim 12, wherein a brightness value curve of the reference pattern sheet is obtained by the measuring device, an amplitude of the brightness value curve is obtained by a difference between an average maximum and an average minimum of the brightness value curve, the first value measured with panel D1$i$ of each first region is determined by a first brightness value obtained by a sum of 10% of the amplitude and the average minimum, and the second value measured with panel D2$i$ of each second region are determined by a second brightness value obtained by a sum of 90% of the amplitude and the average minimum, and the value measured without panel DPi of the predetermined widths of each pair of the first region and the second region is determined by the first brightness value or the second brightness value.

14. The detecting device according to claim 8, wherein the light source is a standard light source comprising D65、D75、D50、TL83、TL84、CWF、U30、U35、F、A、B or C.

15. The detecting device according to claim 8, wherein the measuring device comprises a CCD, a spectrometer or an integrating sphere.

16. The detecting device according to claim 8, wherein the influence factor K is depended on the predetermined illuminance on the reference pattern sheet, the pattern of the reference pattern sheet, the predetermined distance between the reference pattern sheet and the measuring device, and settings of the measuring device.

* * * * *